US008620450B2

(12) United States Patent
Tockman et al.

(10) Patent No.: US 8,620,450 B2
(45) Date of Patent: Dec. 31, 2013

(54) MINIMALLY INVASIVE LEAD SYSTEM FOR VAGUS NERVE STIMULATION

(75) Inventors: Bruce A. Tockman, Scandia, MN (US); Juan Gabriel Hincapie Ordonez, Maple Grove, MN (US); Lili Liu, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 125 days.

(21) Appl. No.: 13/186,203

(22) Filed: Jul. 19, 2011

(65) Prior Publication Data

US 2012/0022617 A1   Jan. 26, 2012

Related U.S. Application Data

(60) Provisional application No. 61/365,483, filed on Jul. 19, 2010.

(51) Int. Cl.
*A61N 1/372* (2006.01)
(52) U.S. Cl.
USPC ............................................................ 607/72
(58) Field of Classification Search
USPC .............................................. 607/72, 74, 108
See application file for complete search history.

(56) References Cited

U.S. PATENT DOCUMENTS

| | | | |
|---|---|---|---|
| 5,251,634 A * | 10/1993 | Weinberg ...................... 600/377 |
| 5,964,702 A | 10/1999 | Grill et al. |
| 7,373,204 B2 | 5/2008 | Gelfand et al. |
| 7,747,334 B2 | 6/2010 | Bly et al. |
| 7,801,603 B2 | 9/2010 | Westlund et al. |
| 7,819,883 B2 | 10/2010 | Westlund et al. |
| 7,917,230 B2 | 3/2011 | Bly |
| 7,949,409 B2 | 5/2011 | Bly et al. |
| 8,244,378 B2 | 8/2012 | Bly et al. |
| 2007/0219596 A1 * | 9/2007 | Dobak, III ...................... 607/46 |
| 2007/0225784 A1 | 9/2007 | Bly et al. |
| 2007/0225786 A1 | 9/2007 | Bly et al. |
| 2008/0033491 A1 | 2/2008 | Zappala et al. |
| 2008/0058874 A1 | 3/2008 | Westlund et al. |
| 2008/0183186 A1 | 7/2008 | Bly et al. |
| 2008/0183187 A1 | 7/2008 | Bly |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 * | 7/2008 | Bly et al. ...................... 607/118 |

(Continued)

OTHER PUBLICATIONS

International Search Report and Written Opinion issued in PCT/US2011/044542, mailed Oct. 4, 2011, 15 pages.

*Primary Examiner* — George Manuel
*Assistant Examiner* — Minh Duc Pham
(74) *Attorney, Agent, or Firm* — Faegre Baker Daniels LLP

(57) ABSTRACT

A system including two neurostimulation leads can be used for stimulating a select region of a nerve within a nerve bundle. For example, two leads can be used to stimulate a select region of the vagus nerve located within a patient's carotid sheath. The first neurostimulation is positioned within the carotid sheath and the second neurostimulation lead is positioned external to the carotid sheath. Each of the first and second neurostimulation leads includes at least one electrode defining an electrode array about the select region of the nerve. The electrode array, and more particularly, the different possible electrode vector combinations provided by the first and second neurostimulation leads facilitate steering of stimulation current density fields as needed or desired between the electrodes to effectively and efficiently treat a particular medical, psychiatric, or neurological disorder.

20 Claims, 8 Drawing Sheets

(56) References Cited

U.S. PATENT DOCUMENTS

| | | |
|---|---|---|
| 2008/0183264 A1 | 7/2008 | Bly et al. |
| 2008/0183265 A1 | 7/2008 | Bly et al. |
| 2008/0234780 A1 | 9/2008 | Smith et al. |
| 2009/0275997 A1* | 11/2009 | Faltys et al. ............. 607/2 |
| 2009/0276025 A1* | 11/2009 | Burnes et al. ............ 607/126 |
| 2010/0023088 A1 | 1/2010 | Stack et al. |

* cited by examiner

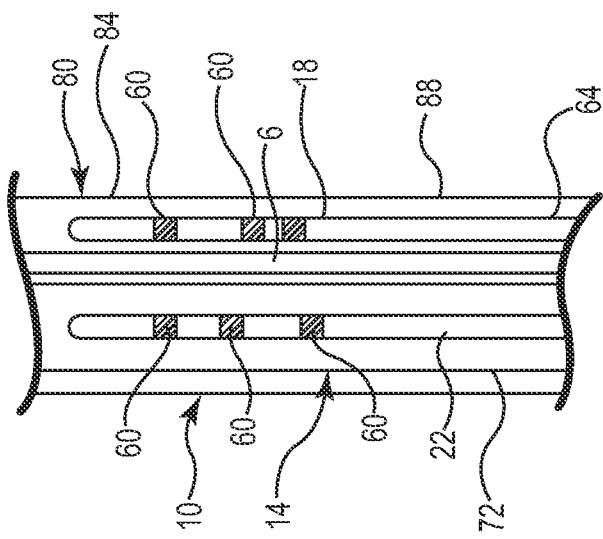
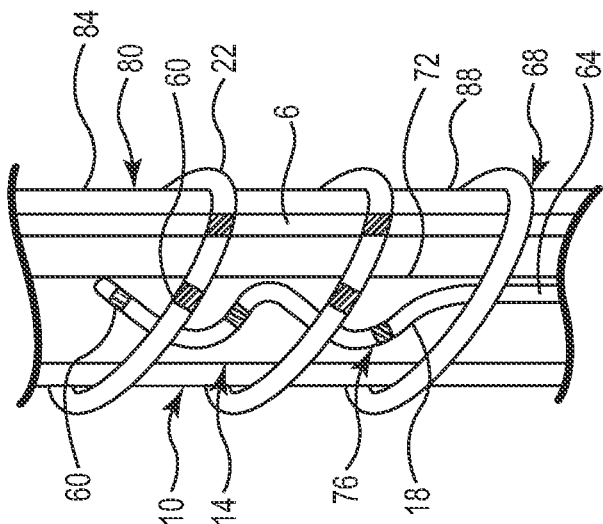
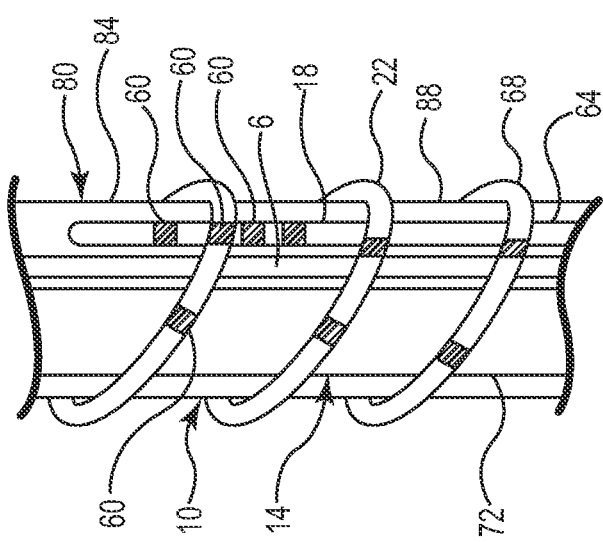
Fig. 2A
Fig. 2B
Fig. 2C

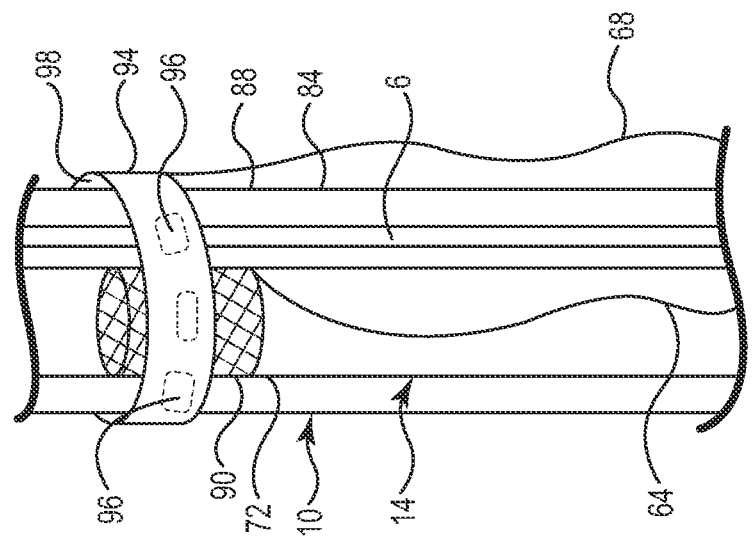
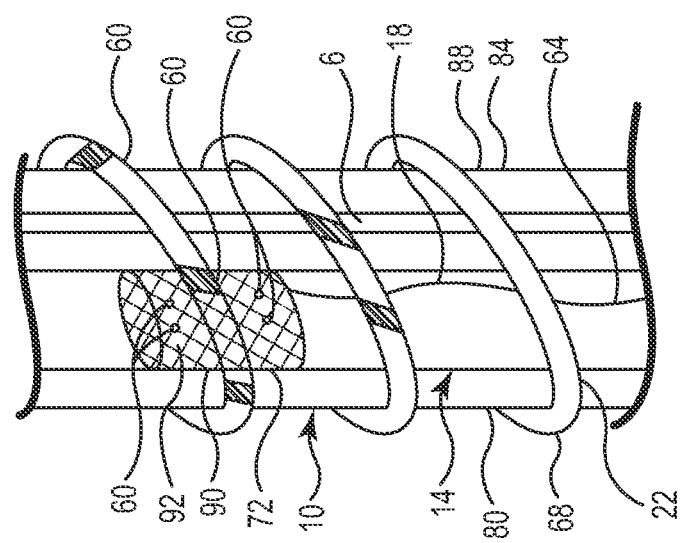

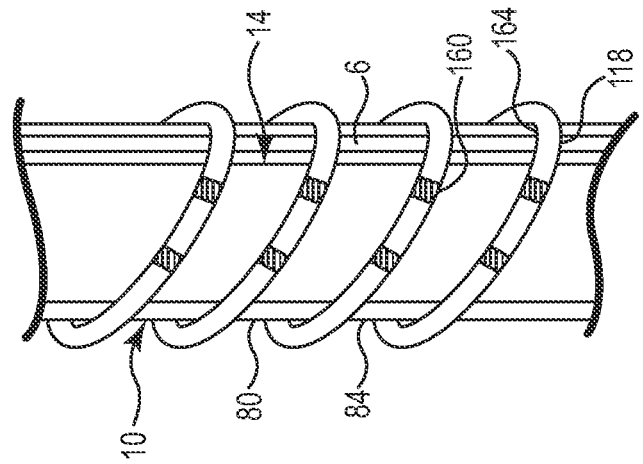
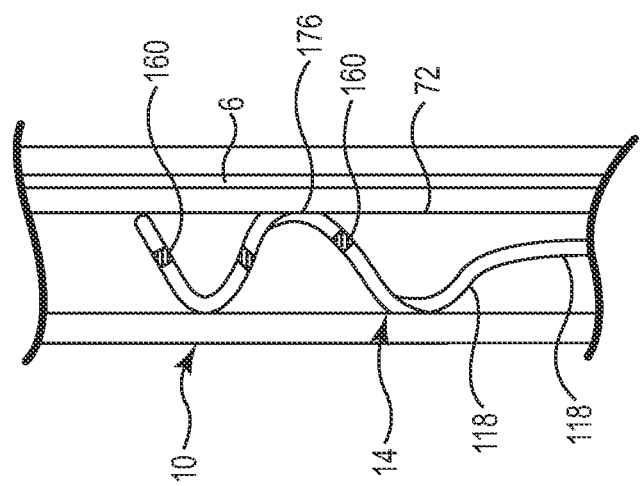
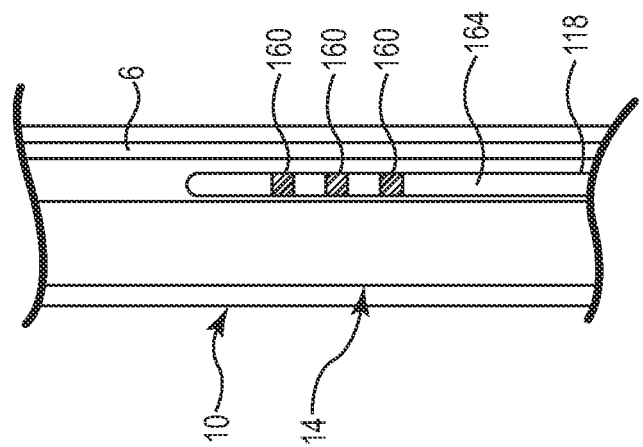

MINIMALLY INVASIVE LEAD SYSTEM FOR VAGUS NERVE STIMULATION

CROSS-REFERENCE TO RELATED APPLICATION

This application claims the benefit under 35 U.S.C. §119(e) to U.S. Provisional Patent Application No. 61/365/483, filed on Jul. 19, 2010, entitled "MINIMALLY INVASIVE LEAD SYSTEM FOR VAGUS NERVE STIMULATION," which is incorporated herein by reference in its entirety.

TECHNICAL FIELD

The present invention is directed to systems and methods for stimulating a region of a nerve within a nerve bundle. More particularly, the present invention is directed to systems and methods for stimulating a region of the vagus nerve within the carotid sheath.

BACKGROUND

The use of nerve stimulation for treating and controlling a variety of medical, psychiatric, and neurological disorders has seen significant growth over the last several decades, including for treatment of heart conditions, epilepsy, obesity, and breathing disorders, among others. For example, modulation of the autonomic balance with neural stimulation has been shown to be possible and have positive clinical benefits, such as protecting the myocardium from further remodeling and predisposition to fatal arrhythmias following a myocardial infarction (MI).

SUMMARY

Example 1 is a system for stimulating a select region of a patient's vagus nerve located within the patient's carotid sheath from a location adjacent the vagus nerve, the system including: a first neurostimulation lead adapted to be deployed at a location adjacent the select region of the vagus nerve within the carotid sheath, the first lead including a lead body extending from a proximal end adapted to be coupled to a pulse generator to a distal portion having a distal end, at least one conductor extending within the lead body from the proximal end towards the distal end, and at least one electrode operatively coupled to the at least one conductor and located on the distal portion, the at least one electrode adapted to deliver an electrical pulse to the vagus nerve; a second neurostimulation lead adapted to be deployed at a stimulation site external to the carotid sheath, the second lead including a lead body extending from a proximal end adapted to be coupled to a pulse generator to a distal portion having a distal end, the distal portion configured to wrap around and contact an external surface of the carotid sheath, a conductor extending within the lead body from the proximal end towards the distal end, and at least one electrode operatively coupled to the at least one conductor located on the distal portion such that when the distal portion is in contact with the external surface of the carotid sheath, the at least one electrode is oriented in a direction towards the vagus nerve; and a pulse generator adapted to send and receive a signal for selectively applying an electrical stimulation to one or more electrodes located on the first and/or second leads.

In Example 2, the system according to Example 1, wherein the distal portion of the second neurostimulation lead comprises a pre-formed spiral, wherein when the second lead is implanted, the spiral is configured to be helically wrapped around the external surface of the carotid sheath such that the at least one electrode is oriented towards the vagus nerve and placed into contact with the carotid sheath, wherein the at least one electrode is adapted to deliver an electrical pulse through the carotid sheath to the vagus nerve.

In Example 3, the system according to any one of Examples 1-2, wherein the distal portion of the second neurostimulation lead comprises a cuff electrode including a resilient cuff having an inner surface and at least one electrical contact located on the inner surface of the resilient cuff, wherein the cuff electrode is configured to be wrapped around the external surface of the carotid sheath such that the at least one electrode contact is oriented towards the vagus nerve and placed into contact with the carotid sheath, wherein the at least one electrode contact is adapted to deliver an electrical pulse through the carotid sheath to the vagus nerve.

In Example 4, the system according to any one of Examples 1-3, wherein the distal portion of the first neurostimulation lead comprises a pre-formed shape configured to orient at least one of the plurality of electrodes in a direction towards the vagus nerve and to stabilize and secure the distal portion of the lead within the carotid sheath at the stimulation site.

Example 5 is a system for stimulating a select region of a patient's vagus nerve located within the patient's carotid sheath from a location adjacent the vagus nerve, the system including: a first neurostimulation lead adapted to be deployed at a location within a region of the patient's internal jugular vein adjacent the select region of the vagus nerve located within the carotid sheath, the first lead including a lead body extending from a proximal end adapted to be coupled to a pulse generator to a distal portion having a distal end, at least one conductor extending within the lead body from the proximal end towards the distal end, and at least one electrode operatively coupled to the at least one conductor and located on the distal portion, the at least one electrode adapted to deliver an electrical pulse to the vagus nerve; a second neurostimulation lead adapted to be deployed at a stimulation site external to the carotid sheath, the second lead including a lead body extending from a proximal end adapted to be coupled to a pulse generator to a distal portion having a distal end, the distal portion configured to wrap around and contact an external surface of the carotid sheath, a conductor extending within the lead body from the proximal end towards the distal end, and at least one electrode operatively coupled to the at least one conductor located on the distal portion such that when the distal portion is in contact with the external surface of the carotid sheath, the at least one electrode is oriented in a direction towards the vagus nerve and the first neurostimulation lead located within the internal jugular vein; and a pulse generator adapted to send and receive a signal for selectively applying an electrical stimulation to one or more electrodes located on the first and/or second leads.

In Example 6, the system according to Example 5, wherein the distal portion of the second neurostimulation lead comprises a pre-formed spiral, wherein when the second lead is implanted, the spiral is configured to be helically wrapped around the external surface of the carotid sheath such that the at least one electrode is oriented towards the vagus nerve and placed into contact with the carotid sheath, wherein the at least one electrode is adapted to deliver an electrical pulse transvascularly through the carotid sheath to the vagus nerve.

In Example 7, the system according to any one of Examples 5-6, wherein the distal portion of the second neurostimulation lead comprises a cuff electrode including a resilient cuff having an inner surface and at least one electrical contact located on the inner surface of the resilient cuff, wherein the cuff electrode is configured to be wrapped around the external surface of the carotid sheath such that the at least one electrode contact is oriented towards the vagus nerve and placed into contact with the carotid sheath, wherein the at least one electrode contact is adapted to deliver an electrical pulse transvascularly through the carotid sheath to the vagus nerve.

In Example 8, the system according to any one of Examples 5-7, wherein the distal portion of the first neurostimulation lead comprises a pre-formed shape configured to orient at least one of the plurality of electrodes in a direction towards the vagus nerve and to stabilize and secure the distal portion of the lead within the carotid sheath at the stimulation site.

Example 9 is a method for stimulating a portion of a patient's vagus nerve located within a carotid sheath, the method including: implanting a first neurostimulation lead within the carotid sheath at a location adjacent the vagus nerve, the first lead including a lead body extending from a proximal end adapted to be coupled to a pulse generator to a distal portion having a distal end, at least one conductor extending within the lead body from a proximal end towards the distal end, and at least one electrode operatively coupled to the at least one conductor located on the distal portion and adapted to deliver an electrical pulse to the vagus nerve; positioning a second medial electrical lead external to the carotid sheath at a position adjacent the vagus nerve and the first neurostimulation lead, the second neurostimulation lead including a lead body extending from a proximal end adapted to be coupled to a pulse generator to a distal portion having a distal end and configured to contact an external surface of the carotid sheath, and at least one electrode located on the distal portion such that when the distal portion is in contact with the external surface of the carotid sheath, the at least one electrode is oriented in a direction towards the vagus nerve and the first neurostimulation lead located within the carotid sheath; selecting an electrode vector for stimulating the vagus nerve; and delivering the electrical stimulation pulse to the vagus nerve.

In Example 10, the method according to Example 9, wherein the step of implanting the first neurostimulation lead within the carotid sheath at a location adjacent the vagus nerve comprises implanting the first neurostimulation lead at a location within the internal jugular vein.

In Example 11, the method according to any one of Examples 9-10, further including the step of evaluating one or more electrode vectors between two or more electrodes located on the distal portions of the first and second neurostimulation leads against a predetermined stimulation threshold value.

In Example 12, the method according to any one of Examples 9-11, wherein the step of positioning the second neurostimulation lead external to the carotid sheath further comprises wrapping the distal portion around an outer circumference of the external sheath such that the at least one electrode is oriented towards the vagus nerve and the first neurostimulation lead, and is in contact with an external surface of the carotid sheath.

In Example 13, the method according to any one of Examples 9-12, wherein the distal portion of the second neurostimulation lead comprises a pre-formed spiral having the at least one electrode located thereon and wherein the step of positioning the second neurostimulation lead external to the carotid sheath further comprises helically wrapping the pre-formed spiral of the distal portion around an outer circumference of the carotid sheath such that the at least one electrode is oriented towards the vagus nerve and the first neurostimulation lead, and is in contact with an external surface of the carotid sheath.

In Example 14, the method according to any one of Examples 9-13, wherein the distal portion of the second neurostimulation lead further comprises a cuff including the at least one electrode located on an internal surface of the cuff and wherein the step of positioning the second neurostimulation lead external to the carotid sheath further comprises engaging the cuff around an outer circumference of the carotid sheath such that the at least one electrode is oriented towards the vagus nerve and the first neurostimulation lead, and is in contact with an external surface of the carotid sheath.

In Example 15, the method according to any one of Examples 9-14, wherein the distal portion of the first medical electrical lead comprises an expandable stent-like structure and the at least one electrode is located on an external surface of the expandable stent-like structure, wherein the step of implanting the first neurostimulation lead within the carotid sheath at the location adjacent the vagus nerve comprises: delivering the first neurostimulation lead to an intravascular location within an internal jugular vein such that the distal portion including the expandable stent-like structure is adjacent the vagus nerve; orienting the at least one electrode located on the external surface of the expandable stent-like structure in a direction towards the vagus nerve; and expanding the expandable stent-like structure such that it contacts and engages a wall of the internal jugular vein securing and stabilizing the lead within the vessel.

In Example 16, the method according to any one of Examples 9-15, wherein the step of implanting the first neurostimulation lead within the carotid sheath comprises delivering the first neurostimulation lead to an intravascular location within an internal jugular vein such that the distal portion is adjacent the vagus nerve and the at least one electrode is oriented in a direction towards the vagus nerve.

In Example 17, the method according to any one of Examples 9-16, wherein the step of implanting the first neurostimulation lead within the carotid sheath comprises implanting the distal portion of the first neurostimulation lead at a location adjacent the vagus nerve between the vagus nerve and an internal jugular vein.

Example 18 is a method for stimulating a portion of a patient's vagus nerve located within a carotid sheath, the method including: implanting a first neurostimulation lead within a patient's internal jugular vein located within the carotid sheath at a location adjacent the vagus nerve, the first lead including a lead body extending from a proximal end adapted to be coupled to a pulse generator to a distal end, one or more of conductors extending within the lead body in a distal direction from a proximal end towards the distal end, and an expandable electrode coupled to the distal end of the lead body and operatively coupled to the one or more electrodes, the expandable electrode adapted to deliver an electrical pulse to the vagus nerve; positioning a second medial electrical lead external to the carotid sheath at a position adjacent the vagus nerve and the first neurostimulation lead, the second neurostimulation lead including a lead body extending from a proximal end adapted to be coupled to a pulse generator to a distal portion having a distal end and configured to contact an external surface of the carotid sheath, and at least one electrode located on the distal portion; electing an electrode vector for stimulating the vagus nerve and; stimulating the vagus nerve.

In Example 19, the method according to Example 18, further including the step of evaluating one or more electrode vectors between two or more electrodes located on the distal portions of the first and second neurostimulation leads against a predetermined stimulation threshold value.

In Example 20, the method according to any one of Examples 18-19, wherein the step of positioning the second neurostimulation lead external to the carotid sheath further comprises wrapping the distal portion around an outer circumference of the external sheath such that the at least one electrode is oriented towards the vagus nerve and the first neurostimulation lead and is in contact with an external surface of the carotid sheath.

In Example 21, the method according to any one of Examples 18-20, wherein the distal portion of the second neurostimulation lead comprises a pre-formed spiral having the at least one electrode located thereon and wherein the step of positioning the second neurostimulation lead external to the carotid sheath further comprises helically wrapping the pre-formed spiral of the distal portion around an outer circumference of the carotid sheath such that the at least one electrode is oriented towards the vagus nerve and the first neurostimulation lead and is in contact with an external surface of the carotid sheath.

In Example 22, the method according to any one of Examples 18-21, wherein the distal portion of the second neurostimulation lead further comprises a cuff including the at least one electrode located on an internal surface of the cuff and wherein the step of positioning the second neurostimulation lead external to the carotid sheath further comprises positioning the cuff around an outer circumference of the carotid sheath such that the at least one electrode is oriented towards the vagus nerve and the first neurostimulation lead and is in contact with an external surface of the carotid sheath.

In Example 23, the method according to any one of Examples 18-22, further including the step of transitioning the expandable electrode from a collapsed configuration suitable for delivery to an expanded configuration, wherein in the expanded configuration the expandable electrode contacts and engages a wall of the internal jugular vein securing and stabilizing the lead within the vessel.

Example 24 is a method for stimulating a portion of a patient's vagus nerve located within a carotid sheath, the method including: positioning a neurostimulation lead within the carotid sheath at a location adjacent the vagus nerve, the lead including a lead body extending from a proximal end adapted to be coupled to a pulse generator to a distal portion having a distal end, at least one conductor extending within the lead body from a proximal end towards the distal end, and a plurality of electrodes operatively coupled to the at least one conductor located on the distal portion and adapted to deliver an electrical pulse to the vagus nerve; orienting at least one of the plurality of electrodes in a direction towards the vagus nerve; selecting an electrode combination for stimulating the vagus nerve; and delivering the electrical stimulation pulse to the vagus nerve.

In Example 25, the method according to Example 24, wherein the neurostimulation lead is implanted at a location within the internal jugular vein adjacent the vagus nerve.

In Example 26, the method according to Examples 24-25, wherein the neurostimulation lead is implanted at a location within the carotid sheath between the vagus nerve and the internal jugular vein.

In Example 27, the method according to Examples 24-26, further including the step of evaluating one or more electrode vectors between two or more electrodes located on the distal portion of the neurostimulation leads against a predetermined stimulation threshold value.

Example 28 is a system for stimulating a select region of a patient's vagus nerve located within the patient's carotid sheath from a location adjacent the vagus nerve, the system including: a neurostimulation lead adapted to be deployed at a location adjacent the select region of the vagus nerve within the carotid sheath, the lead including a lead body extending from a proximal end adapted to be coupled to a pulse generator to a distal portion including a distal end, a plurality of conductors extending within the lead body from the proximal end towards the distal end, and a plurality of electrodes located on the distal portion and operatively coupled to the plurality of conductors in a one to one manner such that each electrode is individually addressable, the at least one electrode adapted to deliver an electrical pulse to the vagus nerve; and a pulse generator adapted to send and receive a signal for selectively applying an electrical stimulation to one or more electrodes located on the first and/or second leads.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2A-2C are schematic views of the distal portions of the two neurostimulation leads shown in FIG. 1 according to some embodiments of the present invention positioned adjacent to a select region of the vagus nerve.

FIG. 3A-3C are schematic views of the distal portions of the two neurostimulation leads shown in FIG. 1 according to other embodiments of the present invention positioned adjacent to a region of the vagus nerve.

FIG. 7A-7C are schematic views of the distal portions of the two neurostimulation leads shown in FIG. 6 according to some embodiments of the present invention positioned adjacent to a select region of the vagus nerve.

Figure 1:
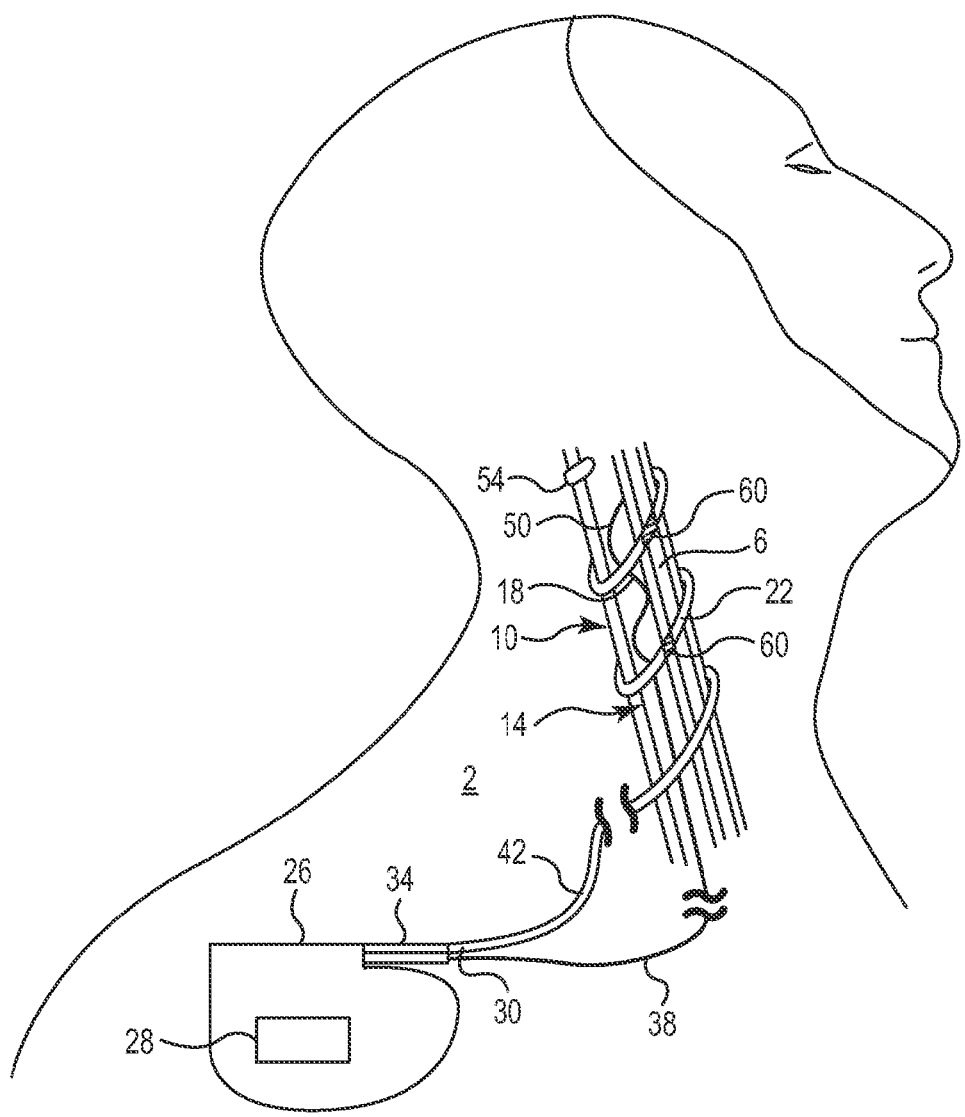
FIG. 1 is a schematic view of a system for stimulating a region of a patient's vagus nerve located within the carotid sheath according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The neural stimulation systems and methods described herein according to the various embodiments can effectively and efficiently be used to treat and control a variety of disorders, such as medical, psychiatric, or neurological disorders, by modulation of autonomic balance. Employing a plurality of electrode bearing leads (e.g., two or more), portions of which are positioned adjacent a nerve trunk of interest, a multiplicity of electrode vector combinations are available to the system for adequately stimulating one or more selected portions of the nerve trunk at low stimulation thresholds and with minimal adverse side-effects.

FIG. 1 shows a system 2 for stimulating a region of a patient's vagus nerve 6 located within the carotid sheath 10. The carotid sheath 10 includes multiple layers of fascia wrapping the common carotid artery (not shown), the internal jugular vein (IJV) 14, and the vagus nerve 6. The system 2 includes a first neurostimulation lead 18, a second neurostimulation lead 22 and an implantable medical device (IMD) 26 such as, for example, a pulse generator. According to various embodiments, the first neurostimulation lead 18 is located within the carotid sheath 10 and the second neurostimulation lead 22 is located external to the carotid sheath 10. In the illustrated embodiment, the first neurostimulation lead 18 is disposed within the IJV 14.

The IMD 26 is adapted to deliver neural stimulation pulses and includes, among other things, a neural stimulation circuit 28. The neural stimulation circuit is adapted to send and receive a signal for selectively applying an electrical stimulation to the vagus nerve via the first and/or second neurostimulation leads 18 and 22. In some embodiments, the neural stimulation circuit 28 includes a programmable memory for storing instructions on which the IMD 26 operates, a processor circuit to process sensed physiologic data or feedback and, in some embodiments, a therapy titration/adjustment circuit which receives the resulting physiologic feedback which can be representative of the efficacy of any applied therapy (e.g., stimulation pulses). Electrical stimulation generated by the IMD 26 (FIG. 1) can be delivered to a select region of the vagus nerve 6 via the first and/or second neurostimulation leads 18 and 22.

The first and second neurostimulation leads 18 and 22 are coupled at their respective proximal ends 30 and 34 to the IMD 26. The proximal ends 30 and 34 of each of the lead bodies 38 and 42 are configured to be operatively connected to the IMD 26 via a connector (not shown). The first and second neurostimulation leads 18 and 22 each include an elongated, insulative lead body 38 and 42 extending from their respective proximal ends 30 and 34 to a distal end 50 and 54, respectively. Each of the lead bodies 38 and 42 is flexible and, in some embodiments, may have a circular cross-section. Alternatively, in other embodiments the lead bodies 38, 42 (or portions thereof) may have non-circular (e.g., elliptical) cross-sectional shapes. In some embodiments, the lead bodies 38 and 42 can include multiple lumens. For example, the lead bodies 38 and 42 can include one or more lumens each configured to receive a conductor and/or a guiding element such as a guidewire or a stylet for delivery and/or implantation of the leads 18 and/or 22.

According to various embodiments, each of the neurostimulation leads 18 and 22 can include a plurality of conductors including individual wires, coils, or cables extending within their respective lead bodies 38 and 42 from the proximal ends 30, 34 towards the distal ends 50, 54 of each of the lead bodies 38 and 42, respectively. The conductors can be insulated and/or molded in place with an insulator such as silicone, polyurethane, ethylene tetrafluoroethylene, or another biocompatible, insulative polymer. In one exemplary embodiment, the conductors have a co-radial design. In this embodiment, each individual conductor is separately insulated and then wound together in parallel to form a single coil. In another exemplary embodiment, the conductors have a co-axial configuration. In still other embodiments, one or more of the conductors is a stranded cable conductor each routed through one of the aforementioned lumens in the lead body 38, 42. In general, the lead can include any combination of conductor types such as for, example, a combination of a coil conductor and a cable conductor.

According to further embodiments of the present invention, each conductor is adapted to be connected to an individual electrode, such as, for example, electrode 60 in a one-to-one manner allowing each electrode 60 to be individually addressable. Additionally, each electrode 60 of the neurostimulation leads 18, 22 can be programmed by the IMD 26 to assume a positive (+) or negative (−) polarity to create a particular stimulation field when current, for example, is applied thereto. Thus, many different vector combinations of programmed anode and cathode electrodes can be used to deliver a variety of current density field waveforms to stimulate a selected region of the vagus nerve 6 without stimulating other nearby structures (e.g., muscles, other nerves, etc.).

According to various embodiments of the present invention, as illustrated in FIGS. 2A-2C and 3A-3C, the distal portions 64 and 68 of each of the first and second neurostimulation leads 18 and 22 are positioned adjacent to a region of the vagus nerve 6 located within the carotid sheath 10. In many embodiments, each of the distal portions 64 and 68 include multiple electrodes (e.g. electrode 60) located thereon. In embodiments including multiple electrodes, the electrodes may form one or more bipolar electrode pairs. In some embodiments, the electrodes can be ring or partial ring electrodes as are generally known in the art. In other embodiments, the electrodes can be stent electrodes, cuff electrodes or sheath electrodes.

In some embodiments, as shown in FIG. 2A, the distal portion 64 of the first neurostimulation lead 18 can be located within the carotid sheath 10 adjacent the vagus nerve 6. In one embodiment, as shown, the first neurostimulation lead 18 can be located within the carotid sheath at a location between the IJV 14 and the vagus nerve 6. The distal portion 64 of the lead 18 can be subcutaneously tunneled to a position adjacent the select region of the vagus nerve 6 located within the carotid sheath 10. The distal portion 64 can be secured at the desired location using sutures or other securing means to prevent dislodgment of the distal portion 64 portion of the lead.

In other embodiments, as shown in FIG. 2B, the distal portion 64 of the first neurostimulation lead 18 can be located within the IJV 14 at a location adjacent the selected region of the vagus nerve 6. The distal portion 64 can be delivered intravascularly to the site within the IJV 14. The electrode(s) 60 located on the distal portion 64 of the lead 18 are adapted to transvascularly deliver an electrical pulse across the vessel wall 72 of IJV 14 to an electrode on a second lead to stimulate the selected region of the vagus nerve 6.

The distal portion 64 of the first neurostimulation lead 18 can be stabilized and secured within the IJV 14 by a variety of techniques. In some embodiments, the distal portion 64 of the first neurostimulation lead 18 can include a pre-formed bias 76 that is adapted to contact and exert a lateral or radial force on the vessel walls 72 of the IJV 14 to stabilize and secure the distal portion within the IJV 14. The pre-formed bias 76 can be used to orient any electrodes 60 located on the distal portion 64 of the lead 18 in a direction towards the vagus nerve 6. In some embodiments, the pre-formed bias 76 is adapted to transition from a collapsed configuration suitable for delivery to an expanded configuration in which the pre-formed bias portion contacts and engages the vessel walls 72 of the IJV 14 securing and stabilizing the distal portion 64 in the IJV 14. The pre-formed bias 76 can include any one of a spiral shape, an S-curve, a sinusoidal curve and the like.

In one embodiment, as shown in FIG. 2B, the pre-formed bias 76 has a spiral shape. In other embodiments, as will be described in greater detail below, the distal portion 64 can include a stent-like member for securing and stabilizing the distal portion 64 in the IJV 14.

According to various embodiments, as shown in FIGS. 2A and 2B, the distal portion 68 of a second neurostimulation lead 22 is located external to the carotid sheath 10 adjacent to the select region of the vagus nerve 6 and the distal portion 64 of the first neurostimulation lead 18 located within the carotid sheath 10. The distal portion 68 of the second neurostimulation lead 22 also includes one or more electrodes 60 and is configured to be wrapped around an outer circumference 80 of the carotid sheath 10. The distal portion 68 is wrapped around the outer circumference 80 of the carotid sheath 10 such that the one or more electrodes 60 located thereon are oriented in a direction towards the vagus nerve 6 located within the carotid sheath 10. In some embodiments, the distal portion 68 is wrapped around the outer circumference 80 of the carotid sheath 10 such that the one or more electrodes 60 are oriented towards the vagus nerve 6 and are in contact with an external surface 84 of the carotid sheath 10. The one or more electrodes 60 are adapted to deliver an electrical pulse across the wall 88 of the carotid sheath 10 to the vagus nerve 6 located within.

In some embodiments, the distal portion 68 can have a pre-formed spiral shape elastically biased such that the distal portion 68 wraps around and engages the external surface 84 of the carotid sheath 10 when implanted. In one embodiment, an inner diameter of the pre-formed spiral is slightly less than an outer diameter of the carotid sheath 10 such that when the distal portion 68 is placed around the external circumference 80 of the carotid sheath 10, the elastic bias causes the distal portion 68 to engage the carotid sheath 10, securing and stabilizing the distal portion 68 of the lead 22 about the carotid sheath 10 such that the electrode(s) is placed into contact with an external surface 88 of the carotid sheath. In other embodiments, sutures may optionally be used to secure the distal portion 68 of the lead 22 in place around the outer circumference of the carotid sheath 10, either by themselves or in combination with the pre-formed elastically biased shape discussed above. In other embodiments, the distal portion 68 can include a cuff or sheath electrode adapted to wrap around and engage the external surface 84 of the carotid sheath 10, as will be described in greater detail below.

In some embodiments, as shown in FIG. 2C, the second neurostimulation lead 22 may be disposed within the carotid sheath 10. In the illustrated embodiment, the second neurostimulation lead 22 is disposed within the IJV 14. In some embodiments, the second neurostimulation lead 22 may be disposed within the carotid sheath 10 but exterior to the IJV 14. The first neurostimulation lead 18 and the second neurostimulation lead 22 may be positioned relative to each other such that the vagus nerve 6 extends between the first neurostimulation lead 18 and the second neurostimulation lead 22. Electrodes 60 located on the first neurostimulation lead 18 and the second neurostimulation lead 22 are adapted to deliver an electrical pulse therebetween to stimulate a selected region of the vagus nerve 6.

Figure 3C:
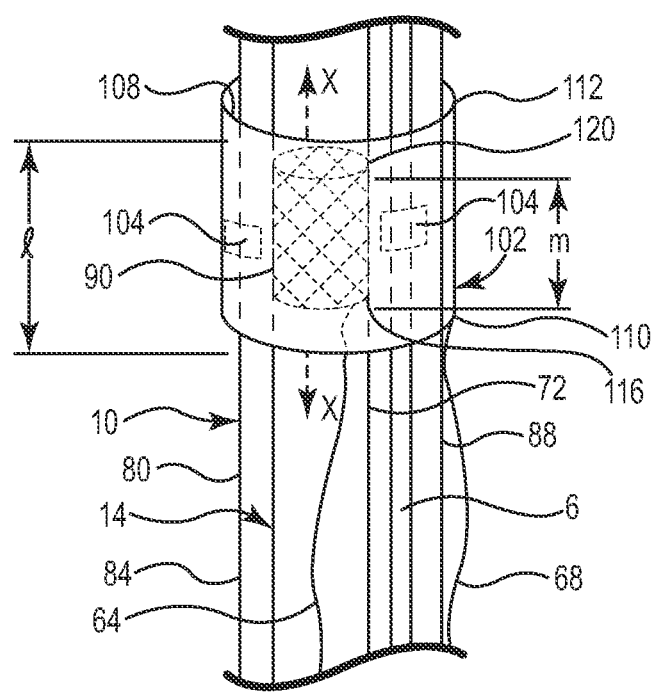

In other embodiments of the present invention, as shown in FIGS. 3A-3C, the distal portion 64 of the first neurostimulation lead 18 includes a stent-like member 90. The stent-like member 90 is adapted to transition from a collapsed configuration suitable for delivery to an expanded configuration. The distal portion 64 of the first stimulation lead 18 including the stent-like member 90 can be delivered intravascularly to a location within the IJV 14 adjacent the selected region of the vagus nerve 6 in a collapsed configuration. The stent-like member 90 is then transitioned from its collapsed configuration to an expanded configuration in which the stent-like member 90 contacts and engages the wall 72 of the IJV 14. In the expanded configuration, the stent-like member 90 contacts and engages the walls 72 of the IJV 14 securing and stabilizing the distal portion 64 of the lead 18 within the IJV 14 at a location adjacent a select region of the vagus nerve 6.

In one embodiment, as shown in FIG. 3A, one or more electrodes 60 are located on an outer surface 92 of the stent-like member 90. The stent-like member 90 can be rotated during the implantation procedure such that at least one of the electrodes 60 located on its outer surface 92 is oriented in a direction towards the vagus nerve 6.

In still other embodiments, as shown in FIGS. 3B and 3C, the stent-like member 90 can be a stent electrode adapted to transvascularly deliver an electrical pulse across the wall 72 of the IJV 14 to the vagus nerve 6. In further embodiments, the stent electrode 90 can be selectively insulated so as to shield other areas of the vagus nerve 6 and surrounding anatomy from undesired stimulation. In one embodiment, for example, the stent electrode 90 can be insulated on an inner surface. In another embodiment, the stent electrode 90 can be operatively coupled to more than one conductor extending within the lead 18 such that one or more regions of the stent electrode 90 can be used to electrically stimulate the vagus nerve 6.

In other embodiments, as shown in FIG. 3B, the distal portion 68 of the second neurostimulation lead 22 can include a cuff electrode 94. The cuff electrode 94 is positioned around the carotid sheath 10 such that it is adjacent the select region of the vagus nerve 6 to be stimulated and the stent-like electrode 90 located within the carotid sheath 10. The cuff electrode 94 is formed of a resilient material and has one or more electrical contacts 96 located on its inner surface 98. The nerve-cuff electrode 94 is sufficiently resilient such that it wraps around and engages an external surface 84 of the carotid sheath 10 such that the one or more electrodes located on an internal surface of the cuff 94 are placed into contact with an external surface 84 of the carotid sheath 10. One or more conductors extending within the lead 22 are coupled to the nerve-cuff electrode 94 to transvascularly deliver an electrical pulse across the wall 88 of the carotid sheath 10 via the one or more electrical contacts 96 to the vagus nerve 6. In some embodiments, the stent-like electrode 90 located within the IJV 14 can have a negative polarity and the nerve-cuff electrode 94 can have a positive polarity, acting as a return electrode.

In some embodiments, as illustrated, the first and second neurostimulation leads 18 and 22 are positioned such that the cuff electrode 94 is axially adjacent the stent-like member 90. In some embodiments, the first and second neurostimulation leads 18 and 22 are positioned such that the cuff electrode 94 is disposed cranial or caudal to the stent-like electrode 90 in order to provide a longitudinal vector between one or more electrodes on the first neurostimulation lead 18 and one or more electrodes on the second neurostimulation lead 22.

In still other embodiments, the distal portion 68 of the second neurostimulation lead 22 can include a sheath electrode 102, as shown in FIG. 3C. The sheath electrode 102 is positioned around the carotid sheath 10 such that it is adjacent the select region of the vagus nerve 6 to be stimulated and the stent-like electrode 90 located within the carotid sheath 10. Like the cuff electrode 94, described above, the sheath electrode 102 is formed of a resilient material and has one or more electrical contacts 104 located on its inner surface 108. The sheath electrode 102 is sufficiently resilient such that it wraps around and engages an external surface 84 of the carotid sheath 10. One or more conductors extending within the lead 22 are coupled to the sheath electrode 102 to transvascularly deliver an electrical pulse across the wall 88 of the carotid sheath 10 via the one or more electrical contacts 104 to the vagus nerve 6. However, unlike the cuff electrode 94, the sheath electrode 102 has an overall length l oriented along a longitudinal axis x that is greater than a length m of the stent electrode 90 located within the carotid sheath 10. In some embodiments, the sheath electrode 102 is placed around an outer circumference 80 of the carotid sheath 10 such that its proximal and distal ends 110 and 112 extend beyond the proximal and distal ends 116 and 120 of the stent-like electrode 90 located within the carotid sheath 10 in order to provide a longitudinal vector. In one embodiment, for example, the sheath electrode can have an overall length ranging from about 5 mm to about 25 mm. In some embodiments, the stent electrode 90 located within the IJV 14 can have a negative polarity and the sheath electrode 102 can have a positive polarity, acting as a return electrode.

In one embodiment, the sheath electrode 102 includes a long band electrode coupled to an inner surface of the sheath electrode 102 where it is adapted to contact the carotid sheath 10. The long band electrode can range in length from about 3 mm to about 10 mm, and may provide a larger radius as a return electrode in order to capture the nerve. A long band electrode may also potentially lower the pacing threshold.

As generally illustrated in FIGS. 2A-2B and 3A-3C, electrical stimulation generated by the IMD 26 (FIG. 1) can be delivered to a select region of the vagus nerve 6 using any combination of the various embodiments of the distal portions 64 and 68 of the neurostimulation leads 18 and 22, described above. Each of the leads 18 and 22 includes one or more electrodes 60, 90, 94 and/or 102 located on their respective distal portions 64 and 68, forming an electrode array (including inter-lead and intra-lead electrode configurations) around the selected region of the vagus nerve 6. The electrode array positioned around the selected region of the vagus nerve 6, and more specifically, the numerous electrode vector combinations (FIG. 4) provided by the first and second neurostimulation leads 18 and 22 facilitate steering of stimulation current density fields as needed or desired between the electrodes to effectively and efficiently treat a particular medical, psychiatric, or neurological disorder. The different combinations of electrodes 60, 90, 94 and/or 102 are used to change the shape of the current density field in and around the selected region of the vagus nerve 6. By using appropriate stimulation parameters (as determined by the IMD 26 (FIG. 1) itself or a physician or other caregiver by way of an external programmer) and electrode locations within the array, a neural stimulation system 2 (FIG. 1) can induce action potentials in the selected region of the vagus nerve 6 that result in the desired treatment effect. In addition, the stimulation current density fields may be steered between two or more electrodes 60, 90, 94 and/or 102 (i.e., an electrode vector) which result in low stimulation thresholds and a minimization of stimulation side-effects.

Figure 4:
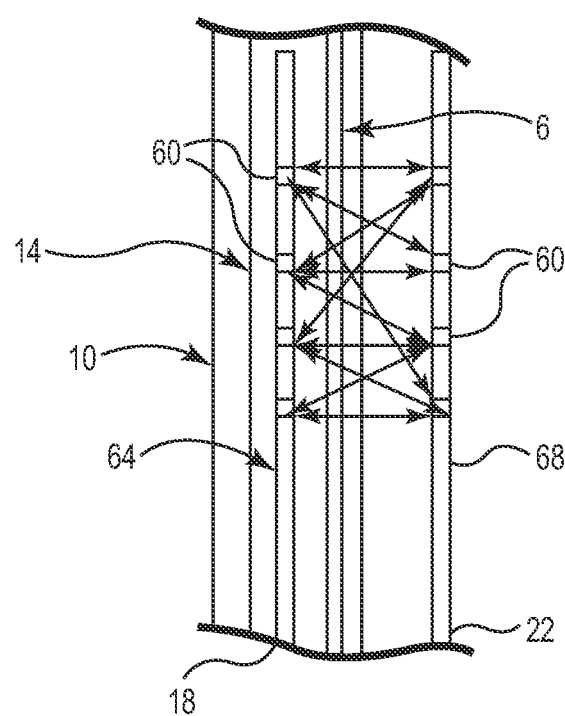
FIG. 4 is a schematic view of various electrode vector combinations that can be generated according to various embodiments of the present invention.

FIG. 4 shows various electrode vector combinations that can be generated by the distal portions 64 and 68 of the two leads 18 and 22 when placed adjacent a select region of a patient's vagus nerve 6 located within the carotid sheath 10, as described in detail above according to the various embodiments of the present invention. The polarity and location of the electrodes 60, 90, 94 and/or 102 chosen to deliver the stimulation current and the parameters of the stimulation current (e.g., amplitude, frequency, burst frequency, duty cycle, or pulse width, etc.) may be based on a status of the one or more sensed physiologic responses, a desire for low stimulation thresholds, the particular disorder the stimulation is meant to treat, or a desire to minimize or abate stimulation side-effects. Additionally, the numerous electrode vector combinations may facilitate the physician or the IMD 26 to recurrently select one or more electrode combinations which optimize or provide an acceptable balance of one or a combination of physiologic feedback responses, a minimal degree of stimulation side-effects, or a low stimulation threshold parameter, among other things.

Figure 5:
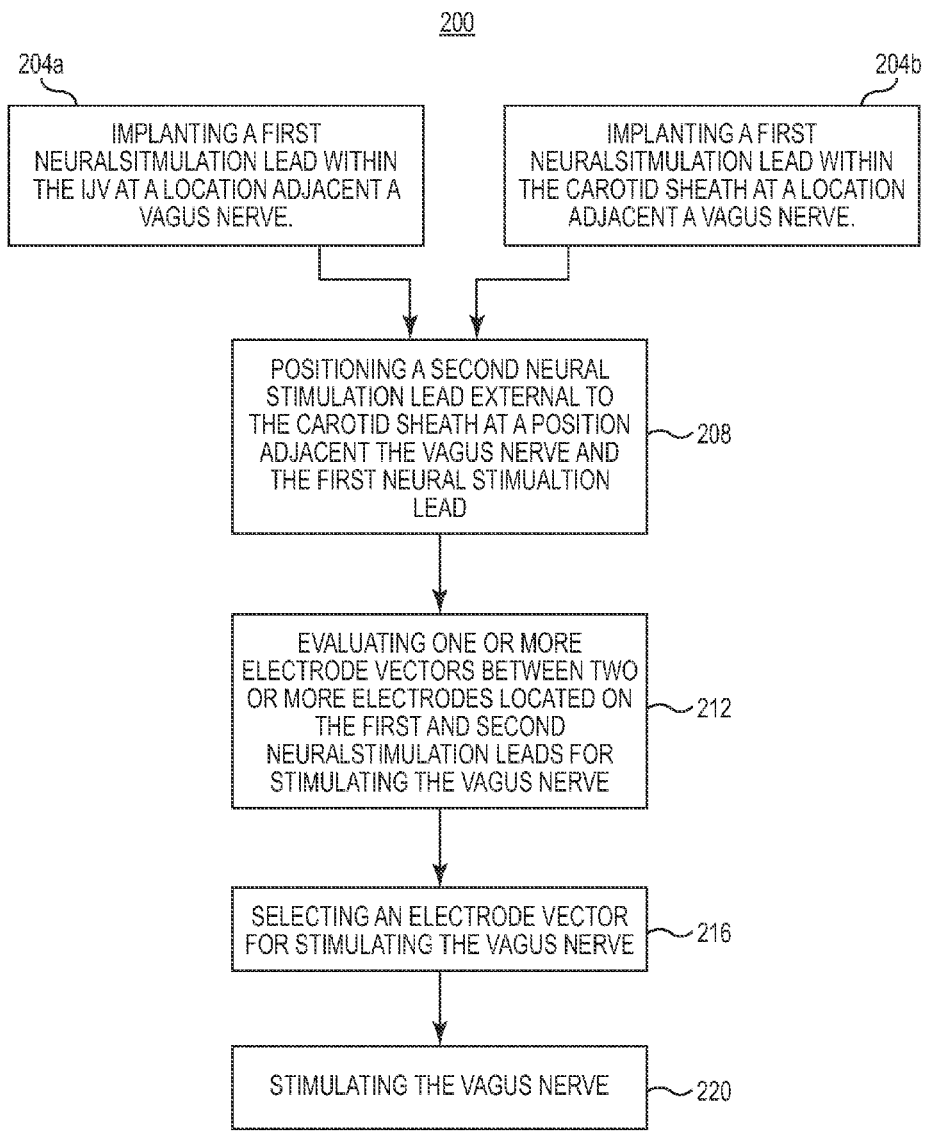
FIG. 5 is a block diagram of a method for stimulating a portion of a patient's vagus nerve located within a carotid sheath according to an embodiment of the present invention.

FIG. 5 is a block diagram outlining a method 200 for stimulating a select region of a patient's vagus nerve 6 located within a carotid sheath 10 using two neurostimulation leads 18 and 22. According to various embodiments, the method 200 includes the step of implanting a first neurostimulation lead 18 within the carotid sheath 10 such that its distal portion 64 is positioned adjacent (or near) to the select region of the vagus nerve 6 (Blocks 204a and 204b). In one embodiment, the distal portion 64 of the first neural stimulation lead 18 including one or more electrodes 60 is implanted within IJV 14 located within the carotid sheath 10 at a location adjacent the select region of the vagus nerve 6 (Block 204a). In another embodiment, the distal portion 64 of the first neural stimulation lead 18 including one or more electrodes 60 located thereon is implanted within the carotid sheath 10 at a location adjacent the select region of the vagus nerve 6 (Block 204b). The first neurostimulation lead 18 can be implanted within the carotid sheath 10 using a variety of techniques including surgical dissection, endoscopy or transvascular delivery techniques under fluoroscopy or other standard visualization techniques.

The method 200 outlined in FIG. 5 also includes positioning a second neurostimulation lead external to the carotid sheath 10 at a location adjacent the select region of the vagus nerve 6 and the first neural stimulation lead 18 (Block 208). More particularly, the distal portion 68 of the second neural stimulation lead 22 including one or more electrodes 60 is positioned external to the carotid sheath at a location adjacent the distal portion 64 of the first neurostimulation lead 18 and the vagus nerve 6 located within the carotid sheath 10 or the in the IJV 14. In some embodiments, as described in greater detail above, the distal portion 68 is configured to engage the external surface of the carotid sheath such that when the distal portion 68 is in contact with the carotid sheath at least one electrode 60 is oriented in a direction towards the vagus nerve 6 and the distal portion 64 of the first neurostimulation lead 18. For example, in some embodiments, the distal portion 68 of the second neural stimulation lead 22 can be helically wrapped around the carotid sheath.

Once the two leads and their respective distal portions 64, 68 have been positioned adjacent to the select region of the vagus nerve 6, one or more electrode vectors established between two or more sets of electrodes located the distal portions of the first and second neurostimulation leads 18 and 22 are evaluated for stimulating the vagus nerve (Block 212). The electrode vectors are evaluated against a predetermined stimulation threshold for their ability to stimulate the vagus nerve and produce a desired response. An electrode vector for stimulating the vagus nerve 6 is then selected using the data generated during the evaluation step, and the vagus nerve 6 is then stimulated (Blocks 216 and 220).

Figure 6:
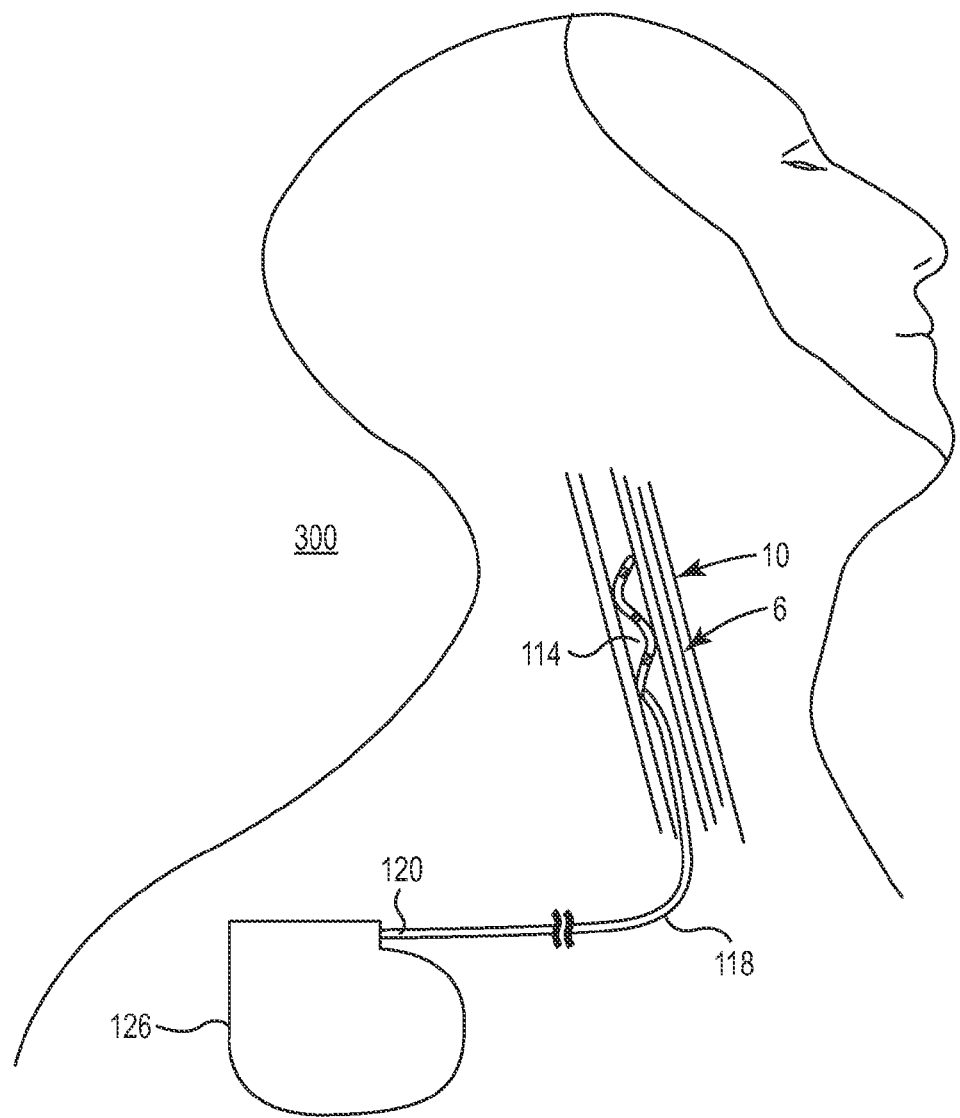
FIG. 6 is a schematic view of a system for stimulating a region of a patient's vagus nerve located within the carotid sheath according to an embodiment of the present invention.

In still other embodiments of the present invention a single lead system 300, as shown in FIG. 6, can be used to stimulate a region of the vagus nerve 6. According to various embodiments, the system 300 includes a neurostimulation lead 118 coupled at its proximal end 120 to an IMD 126 via a connector (not shown). The neurostimulation lead 118 can have many or all of the same features of the leads 18 and 22, discussed above according to the various embodiments.

According to various embodiments of the present invention, as illustrated in FIGS. 7A-7C, the distal portion 164 of the lead 118 can be positioned adjacent to a region of the vagus nerve 6 located within the carotid sheath 10. In many embodiments, the distal portion 164 can include multiple electrodes (e.g. electrode 160) located thereon. In embodiments including multiple electrodes, the electrodes may form one or more bipolar electrode pairs. In some embodiments, the electrodes can be ring or partial ring electrodes as are generally known in the art. In other embodiments, the electrodes can be stent electrodes, cuff electrodes or sheath electrodes.

In some embodiments, as shown in FIG. 7A, the distal portion 164 of the neurostimulation lead 118 can be located within the carotid sheath 10 at a location between the IJV 14 and the vagus nerve 6. In one embodiment, the distal portion 164 of the lead 118 can be subcutaneously tunneled to a position adjacent the select region of the vagus nerve 6 located within the carotid sheath 10. The distal portion 64 can be secured at the desired location using sutures or other securing means to prevent dislodgment of the distal portion 164 portion of the lead. In still another embodiment, the distal portion 164 of the lead 118 can include a nerve cuff (not shown) adapted to be placed around the vagus nerve 6.

In other embodiments, as shown in FIG. 7B, the distal portion 164 of the first neurostimulation lead 118 can be located within the IJV 14 at a location adjacent the selected region of the vagus nerve 6. The distal portion 164 can be delivered intravascularly to the site within the IJV 14. The electrode(s) 160 located on the distal portion 64 of the lead 18 are adapted to transvascularly deliver an electrical pulse across the vessel wall 72 of IJV 14 to stimulate the selected region of the vagus nerve 6.

The distal portion 164 of the first neurostimulation lead 118 can be stabilized and secured within the IJV 14 by a variety of techniques. In some embodiments, the distal portion 164 of the first neurostimulation lead 118 can include a pre-formed bias 176 that is adapted to contact and exert a lateral or radial force on the vessel walls 72 of the IJV 14 to stabilize and secure the distal portion within the IJV 14. The pre-formed bias 176 can be used to orient any electrodes 160 located on the distal portion 164 of the lead 118 in a direction towards the vagus nerve 6. In some embodiments, the pre-formed bias 176 is adapted to transition from a collapsed configuration suitable for delivery to an expanded configuration in which the pre-formed bias portion contacts and engages the vessel walls 72 of the IJV 14 securing and stabilizing the distal portion 164 in the IJV 14. The pre-formed bias 176 can include any one of a spiral shape, an S-curve, a sinusoidal curve and the like. In one embodiment, as shown in FIG. 7B, the pre-formed bias 76 has a spiral shape. In other embodiments, the distal portion 164 can include a stent-like member for securing and stabilizing the distal portion 64 in the IJV 14, as described in detail above in reference to FIG. 3A.

In other embodiments, the distal portion 164 of the lead 118 can be located external to the carotid sheath18 adjacent to the select region of the vagus nerve 6. In one embodiment, the distal portion 164 of the lead 118 is configured to be helically wrapped around an outer circumference surface 80 of the carotid sheath 10. The distal portion 164 is wrapped around the outer circumference 80 of the carotid sheath 10 such that the one or more electrodes 160 located thereon are oriented in a direction towards the vagus nerve 6 located within the carotid sheath 10. In some embodiments, the distal portion 164 is wrapped around the outer circumference 80 of the carotid sheath 10 such that the one or more electrodes 160 are oriented towards the vagus nerve 6 and are in contact with an external surface 84 of the carotid sheath 10. The one or more electrodes 160 are adapted to transvascularly deliver an electrical pulse across the wall 88 of the carotid sheath 10 to the vagus nerve 6 located within.

In some embodiments, the distal portion 164 can have a pre-formed spiral shape elastically biased such that the distal portion 164 wraps around, engages and applies a compressive force to the external surface 84 of the carotid sheath 10 when implanted. In one embodiment, an inner diameter of the pre-formed spiral is slightly less than an outer diameter of the carotid sheath 10 such that when the distal portion 164 is placed around the external circumference 80 of the carotid sheath 10, the elastic bias causes the distal portion 164 to engage the carotid sheath 10, securing and stabilizing the distal portion 164 of the lead 22 about the carotid sheath 10. In other embodiments, sutures may optionally be used to secure the distal portion 164 of the lead 118 in place about the outer circumference of the carotid sheath 10, either by themselves or in combination with the pre-formed elastically biased shape discussed above. In other embodiments, the distal portion 164 can include a cuff or sheath electrode adapted to wrap around and engage the external surface 84 of the carotid sheath 10, as described in greater detail above in reference to FIGS. 3B and 3C.

Once the distal portion 164 is positioned and secured at a location adjacent to the region of the vagus nerve 6, electrical stimulation generated by the IMD 126 (FIG. 6) can be delivered to a select region of the vagus nerve 6 using any combination of electrodes located on the distal portion 164 of the lead 118 forming an intra-lead electrode array.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system for stimulating a select region of a patient's vagus nerve located within the patient's carotid sheath from a location adjacent the vagus nerve, the system comprising:

a first neurostimulation lead adapted to be deployed at a location adjacent the select region of the vagus nerve within the carotid sheath, the first lead comprising a lead body extending from a proximal end adapted to be coupled to a pulse generator to a distal portion having a distal end, at least one conductor extending within the lead body from the proximal end towards the distal end, and at least one electrode operatively coupled to the at least one conductor and located on the distal portion, the at least one electrode adapted to deliver an electrical pulse to the vagus nerve;

a second neurostimulation lead adapted to be deployed at a stimulation site external to the carotid sheath, the second lead comprising a lead body extending from a proximal end adapted to be coupled to a pulse generator to a distal portion having a distal end, the distal portion configured to wrap around and contact an external surface of the carotid sheath, a conductor extending within the lead body from the proximal end towards the distal end, and at least one electrode operatively coupled to the at least one conductor located on the distal portion such that when the distal portion is in contact with the external surface of the carotid sheath, the at least one electrode is oriented in a direction towards the vagus nerve; and a pulse generator adapted to send and receive a signal for selectively applying an electrical stimulation to an electrode array defined by the one or more electrodes located on the first and second leads, wherein the electrode array is configured such that electrical stimulation applied to the electrode array facilitates steering of stimulation current density fields between the electrodes in and around the select region of the vagus nerve as desired to treat a particular medical, psychiatric or neurological disorder, and wherein different combinations of electrodes in the electrode array may be selected so as to change the stimulation current density fields in and around the select region of the vagus nerve.

2. The system of claim 1, wherein the distal portion of the second neurostimulation lead comprises a pre-formed spiral, wherein when the second lead is implanted, the spiral is configured to be helically wrapped around the external surface of the carotid sheath such that the at least one electrode is oriented towards the vagus nerve and placed into contact with the carotid sheath, wherein the at least one electrode is adapted to deliver an electrical pulse through the carotid sheath to the vagus nerve.

3. The system of claim 1, wherein the first neurostimulation lead is adapted to be deployed within an internal jugular vein extending through the carotid sheath.

4. The system of claim 3, wherein the distal portion of the first neurostimulation lead comprises a pre-formed shape configured to orient at least one of the plurality of electrodes in a direction towards the vagus nerve and to stabilize and secure the distal portion of the lead within the internal jugular vein at the stimulation site.

5. The system of claim 1, wherein the first neurostimulation lead is adapted to be deployed within the carotid sheath exterior to an internal jugular vein.

6. A system for stimulating a select region of a patient's vagus nerve located within the patient's carotid sheath from a location adjacent the vagus nerve, the system comprising:

a first neurostimulation lead adapted to be deployed at a location within a region of the patient's internal jugular vein adjacent the select region of the vagus nerve located within the carotid sheath, the first lead comprising a lead body extending from a proximal end adapted to be coupled to a pulse generator to a distal portion having a distal end, at least one conductor extending within the lead body from the proximal end towards the distal end, and at least one electrode operatively coupled to the at least one conductor and located on the distal portion, the at least one electrode adapted to deliver an electrical pulse to the vagus nerve;

a second neurostimulation lead adapted to be deployed at a stimulation site adjacent the select region of the vagus nerve, the second lead comprising a lead body extending from a proximal end adapted to be coupled to a pulse generator to a distal portion having a distal end, a conductor extending within the lead body from the proximal end towards the distal end, and at least one electrode operatively coupled to the at least one conductor located on the distal portion such that when the distal portion is positioned relative to the vagus nerve, the at least one electrode is oriented in a direction towards the vagus nerve and the first neurostimulation lead located within the internal jugular vein; and a pulse generator adapted to send and receive a signal for selectively applying an electrical stimulation to an electrode array defined by the one or more electrodes located on the first and second leads, wherein the electrode array is configured such that electrical stimulation applied to the electrode array facilitates steering of stimulation current density fields between the electrodes in and around the select region of the vagus nerve as desired to treat a particular medical, psychiatric or neurological disorder, and wherein different combinations of electrodes in the electrode array may be selected so as to change the stimulation current density fields in and around the select region of the vagus nerve.

7. The system of claim 6, wherein the distal portion of the second neurostimulation lead is configured to wrap around and contact an external surface of the carotid sheath.

8. The system of claim 7, wherein the distal portion of the second neurostimulation lead comprises a pre-formed spiral, wherein when the second lead is implanted, the spiral is configured to be helically wrapped around the external surface of the carotid sheath such that the at least one electrode is oriented towards the vagus nerve and placed into contact with the carotid sheath, wherein the at least one electrode is adapted to deliver an electrical pulse transvascularly through the carotid sheath to the vagus nerve.

9. The system of claim 6, wherein the second neurostimulation lead is adapted for deployment within the carotid sheath.

10. The system of claim 6, wherein the distal portion of the first neurostimulation lead comprises a pre-formed shape configured to orient at least one of the plurality of electrodes in a direction towards the vagus nerve and to stabilize and secure the distal portion of the lead within the carotid sheath at the stimulation site.

11. The system of claim 6, wherein the distal portion of the first neurostimulation lead comprises a stent-like expandable fixation member.

12. The system of claim 11, wherein the stent-like expandable fixation member includes an electrode.

13. The system of claim 6, wherein the distal portion of the second neurostimulation lead comprises a cuff electrode.

14. A method for stimulating a portion of a patient's vagus nerve located within a carotid sheath, the method comprising:

implanting a first neurostimulation lead within the carotid sheath at a location adjacent the vagus nerve, the first lead comprising a lead body extending from a proximal end adapted to be coupled to a pulse generator to a distal portion having a distal end, at least one conductor extending within the lead body from a proximal end towards the distal end, and at least one electrode operatively coupled to the at least one conductor located on the distal portion and adapted to deliver an electrical pulse to the vagus nerve;

positioning a second neurostimulation lead at a position adjacent the vagus nerve and the first neurostimulation lead, the second neurostimulation lead comprising a lead body extending from a proximal end adapted to be coupled to a pulse generator to a distal portion having a distal end, and at least one electrode located on the distal portion such that when the distal portion is positioned adjacent the carotid sheath, the at least one electrode is oriented in a direction towards the vagus nerve and the first neurostimulation lead located within the carotid sheath;

positioning the first and second neurostimulation leads such that the one or more electrodes on the first and second neurostimulation leads define an electrode array that is configured such that electrical stimulation applied to the electrode array results in an electrode vector between the electrodes in and around the vagus nerve as desired to treat a particular medical, psychiatric or neurological disorder, and wherein different combinations of electrodes in the electrode array may be selected so as to change the electrode vector that stimulates the vagus nerve;

selecting an electrode vector for stimulating the vagus nerve; and delivering the electrical stimulation pulse to the vagus nerve.

15. The method of claim 14, wherein implanting the first neurostimulation lead within the carotid sheath comprises implanting the distal portion of the first neurostimulation lead within an internal jugular vein.

16. The method of claim 14, wherein implanting the first neurostimulation lead within the carotid sheath comprises implanting the distal portion of the first neurostimulation lead at a location adjacent the vagus nerve between the vagus nerve and an internal jugular vein.

17. The method of claim 14, wherein positioning the second neurostimulation lead comprises positioning the second neurostimulation lead external to the carotid sheath.

18. The method of claim 17, further comprising wrapping the distal portion around an outer circumference of the external sheath such that the at least one electrode is oriented towards the vagus nerve and the first neurostimulation lead, and is in contact with an external surface of the carotid sheath.

19. The method of claim 14, wherein positioning the second neurostimulation lead comprises positioning the second neurostimulation lead within the carotid sheath.

20. The method of claim 14, further comprising the step of evaluating one or more electrode vectors between two or more electrodes located on the distal portions of the first and second neurostimulation leads against a predetermined stimulation threshold value.

* * * * *